United States Patent [19]

Mynard et al.

[11] 4,347,244
[45] Aug. 31, 1982

[54] GANGLIOSIDE CONTAINING COMPOSITIONS FOR TREATING DIARRHEA

[75] Inventors: Marie-Claude Mynard, Sainte Foy-les-Lyon; Jean-Louis Tayot, La Tour de Salvagny, both of France

[73] Assignee: Societe Anonyme dite: Institut Merieux, Lyons, France

[21] Appl. No.: 217,114

[22] PCT Filed: Mar. 17, 1980

[86] PCT No.: PCT/FR80/00037

§ 371 Date: Nov. 13, 1980

§ 102(e) Date: Nov. 13, 1980

[87] PCT Pub. No.: WO80/01875

PCT Pub. Date: Sep. 18, 1980

[30] Foreign Application Priority Data

Mar. 16, 1979 [DE] Fed. Rep. of Germany ....... 2910509
Mar. 16, 1979 [FR] France ................................. 79 06732

[51] Int. Cl.$^3$ ............................................ A61K 31/70
[52] U.S. Cl. .................................................... 424/180
[58] Field of Search ......................................... 424/180

[56] References Cited

U.S. PATENT DOCUMENTS 3,101,299  8/1963  Ferrand ................................ 424/357
3,400,197  9/1968  Lippmann ............................ 424/357
3,627,885 12/1971  Rondelet ............................. 424/357

OTHER PUBLICATIONS

Tayot et al.–Chem. Abst., vol. 90 (1979), p. 81812z (original article pub. 1978).

*Primary Examiner*—Sam Rosen
*Attorney, Agent, or Firm*—Cushman, Darby & Cushman

[57] ABSTRACT

The invention is concerned with a medium onto which is fixed a ganglioside or ganglioside derivative having an affinity for the toxins produced by the bacteria responsible for diarrheas and in particular for the cholera toxin.

23 Claims, No Drawings

GANGLIOSIDE CONTAINING COMPOSITIONS FOR TREATING DIARRHEA

The present invention concerns a new medicine and the pharmaceutical compositions containing it.

More specifically, the invention concerns a new medicine making it possible to treat prophylactically or curatively acute diarrhea, and in particular cholera.

The medicine of the invention is characterized by the fact that it consists of a medium onto which is fixed a ganglioside or ganglioside derivative having an affinity for the toxins produced by the bacteria responsible for diarrhea and in particular for the choleraic toxin, said medium being compatible with oral administration.

The usable media are all those which are compatible with oral use, having a strong and preferably irreversible affinity for the gangliosides or which can be chemically linked with the gangliosides. They should preferably have a high specific surface (use of porous media). They must also allow satisfactory contact between the ganglioside and the toxins to be neutralized.

The media are chosen for example from the group consisting of: activated carbon, latex, polysaccharides such as cellulose, modified or not, and porous mineral media such as silica, alumina, titanium oxide, or their natural or synthetic derivatives such as glass, silicates, kaolin, etc., possibly bearing polysaccharides.

Preferably, the medium is pharmaceutical-quality activated carbon, and in particular carbon marketed under the name ACTI-CARBONE WL 3S.

Generally speaking, all pharmaceutical-quality carbons are suitable.

It is known that among the various gangliosides the $G_{M1}$ ganglioside and certain of its derivatives have a strong and specific biochemical affinity for choleraic toxins and structurally related toxins. This affinity is also observed with certain derivatives of the $G_{M1}$ ganglioside. This is in particular the case with the $G_{M1}$ lysoganglioside. The $G_{M1}$ lysoganglioside is obtained by alkaline hydrolysis of the $G_{M1}$ ganglioside according to the process described by HOLMGREN, MÄSSON and SVENNER-HOLM, Medical Biology (1974), 52, 229–233. This alkaline hydrolysis is aimed at transforming the two N-acetyl functions and the N-actyl function of the $G_{M1}$ ganglioside into an $NH_2$ amine function.

Other ganglioside derivatives also have an affinity for the choleraic toxin.

In the present application, by convention "derivative of the $G_{M1}$ ganglioside" or "$G_{M1}$" will designate any ganglioside derivative which has an affinity for the choleraic toxin, and in particular the products resulting from a partial or total hydrolysis of the N-acyl or N-acetyl groupings into $NH_2$ groupings of the $G_{M1}$ ganglioside, but also the mono- or a-sialo-gangliosides resulting from the acid treatment of the gangliosides or their derivatives (in particular their derivatives resulting from total or partial hydrolysis of the N-actyl or N-acetyl groupings).

The products of partial de-acylation of the gangliosides have free-amine groupings which can be brought to light by a positive reaction in the ninhydrine test and are mobile in chromatography on a thin layer of silica gel in the chloroform-methanol-water system (60:32:7), and have the specific affinity properties of the gangliosides from which they derive. They maintain these properties of affinity even if they are coupled to solid media by means of the amine groupings appearing upon partial deacylation.

They are prepared by treatment of the gangliosides with a basic aqueous solution at a temperature between 0° and 120° C., said temperature being lower as the medium is more basic. For a final solution with alkalinity comparable to normal soda or potassium, it is important not to exceed 100° C. For an alkalinity comparable to deci-normal soda or potassium, it is important not to exceed 120° C.

The reaction time must be sufficient for the appearance of free-amine groupings, but the reaction must be halted before total de-acylation. The reaction time can be easily determined in each case by simple experimentation, using for example the ninhydrine test, seeking an intermediate coloration with an intensity lower than that obtained after complete de-acylation. Generally, the reaction time varies between 30 minutes and 24 hours.

The reaction solvent is either water or a mixture of water and organic solvents. Among the organic solvents we shall mention alcohols such as butanol.

Among the usable bases, we shall mention those which are capable of giving a pH of 9 to 14 in water, and in particular of dissolving the selected ganglioside in normal soda or potassium, with this solution being incubated at 60° C. for 2 hours.

As for the products of total de-acylation of the gangliosides, they are prepared by the processes described in the literature.

It has further been discovered that certain bacteria responsible for acute diarrhea, and in particular certain strains of Escherichia coli, are likely to give off enterotoxins which can be bound to the ganglioside derivatives, in particular to the $G_{M1}$ ganglioside.

Generally, the medicine of the invention contains about 1 to 20 micromoles, and in particular about 3 to 10 micromoles, of gangliosides or ganglioside derivatives per gram of medium.

The medium is generally in the form of a particulate material. The dimensions of the particles in the medium material may vary for example from 0.1 to 1000 micrometers.

The invention also concerns a process for preparing the medicine as defined above. This process is characterized by the fact that the $G_{M1}$ ganglioside and/or its derivatives is fixed onto the medium. This fixation may be achieved either by creating a chemical bond, or by making use of any phenomenon of affinity, for example a phenomenon of adsorption.

In this latter case, it is sufficient to place the medium in contact with a solution of gangliosides or ganglioside derivatives.

Such a solution of gangliosides or ganglioside derivatives can in particular be obtained according to the process described in the French patent application No. 76.23176.

After a sufficient contact time to couple the ganglioside to the medium, the coupled product is separated out by centrifuging, then the precipitate obtained is washed.

As a variant, it is possible, for example, before or after centrifuging, to transform the ganglioside into another ganglioside derivative, in particular by acid hydrolysis which makes it possible to change the majority of the polysialogangliosides into monosialogangliosides.

Generally, the fixation of the ganglioside or its derivatives onto the medium is sufficiently strong. If need be it can be complemented by a chemical coupling reaction.

As for the active carbon particles, simple fixation by adsorption is sufficient. The $G_{M1}$ ganglioside or its derivatives are easily adsorbed.

In order to fix the $G_{M1}$ ganglioside onto latex particles, an alkaline pH is used, while this alkaline pH is not necessary to couple the $G_{M1}$ lysoganglioside. When the latex carries $NH_2$ functions, it is useful to pretreat it with a carbonylated derivative, such treatment promoting the fixation of the ganglioside or its derivatives.

The ganglioside derivative can be fixed for example onto polysaccharide particles. The expression "polysaccharide" in the present application encompasses the modified polysaccharides. These polysaccharides are in particular dextran, celluloses, starch, agarose, etc., or modified polysaccharides, in particular dialkylaminoalkyl- or di(hydroxyalkyl)aminoalkyl-polysaccharides such as diethylaminoethyl dextran, diethylaminoethyl cellulose, etc. The ganglioside derivative is fixed onto the polysaccharides by means of coupling agents such as diepoxides, dicarbonylates, epihalohydrines, or cyanogen bromide, according to known methods.

The polysaccharides can also be used not in the form of particles but in the form of a covering on mineral particles, in particular of mineral oxides such as those mentioned above.

The porous mineral particles covered with polysaccharides or modified polysaccharides may be in particular those described in French patent application No. 76.23176, or those described in French patent application No. 77.28163.

The mineral particles covered with polysaccharides according to French patent application No. 76.23176 consist of a porous mineral medium such as a porous mineral oxide, directly covered on its surface by an amino-polysaccharidic polymer.

The porous mineral medium may be silica, alumina, magnesia, titanium oxide, or their synthetic or natural derivatives such as glass, borosilicates, silicates, kaolin, etc.

The amino-polysaccharidic polymer is fixed onto the porous mineral medium by gluing.

The internal surface of the porous mineral medium is for example less than or equal to 100 m²/g, and if possible between 5 and 80 m²/g. The average pore diameter is preferably greater than or equal to 25 nm, and if possible between 50 and 1000 nm. For larger surfaces or smaller pore diameters, the internal surface of the medium becomes inaccessible to the polysaccharidic polymer. The mineral porous medium is for example silica or alumina, and preferably a porous silica medium of an anionic nature obtained according to the processes described in French patent Nos. 1.473.239, 1.473.240, 1.475.929, 1.482.867, such as the porous silicas marketed by RHONE-POULENC CHIMIE FINE under the names SPHEROSIL XOB 030, XOB 015, XOB 005, and XOC 005.

The amino-polysaccharidic polymer which serves to impregnate and cover the internal surface of the mineral porous medium must have a pronounced cationic nature and have good hydrophilic qualities. It must have a molecular weight at least equal to $10^4$ daltons, and if possible be between $10^5$ and $10^6$. It may have any formula, and in particular it may be an amino-derivative of dextran, starch, cellulose, agarose or a natural or synthetic polymer of all known oses.

The amine functions of the polysaccharidic polymer may be primary, secondary, tertiary or possibly quaternary.

The amino-polysaccharidic polymer may in particular correspond to the formula $$R-(CH_2)_n-NR_1(R_2)$$

in which:

R represents a polysaccharide remnant such as for example a dextran, starch, cellulose or agarose remnant, n is a whole number from 1 to 10 and preferably 2 to 5, $R_1$ and $R_2$, identical or different, represent an inferior alkyl or hydroxyalkyl radical, for example the following radicals:

$$-CH_3, -CH_2-CH_3, -CH_2OH, -CH_2-CH_2OH$$
$$\text{or} -CH_2-CHOH-CH_3,$$

these polymers being able to be quaternized by means of a classic quaternizing agent such as the alkyl or hydroxyalkyl halogenides, dimethyl sulfate, etc.

Among the polymers of this type, we may in particular mention the compounds known under the names DEAE DEXTRAN (diethylamino ethyl dextran) with a molecular weight of 500,000 and QAE DEXTRAN (diethylamino ethyl dextran, quaternized) sold by the PHARMACIA company, and the compound known by the name DEAE starch (diethylamino ethyl starch) as well as the cationic starches such as those sold under the commercial name CATO by the ROQUETTE NATIONAL company.

The amino-polysaccharidic polymer can also be reticulated by means of a reticulating agent, for example a dicarbonylated compound, a diepoxide such as 1-4 butanedioldiglycidyl-ester, or epichlorhydrine or epibromhydrine.

The ganglioside derivatives are fixed onto the porous media thus covered, for example by means of the coupling agents already mentioned above.

The porous mineral particles covered with polysaccharides, modified or not, according to French patent application No. 77.28163 consist of a porous mineral medium covered by a polysaccharidic polymer, or by a modified polysaccharidic polymer, for example an amine polysaccharide such as mentioned above, said polysaccharidic covering being stabilized if necessary by reticulation, and on said polysaccharidic or modified polysaccharidic covering is found grafted a ganglioside derivative with the schematic formula $R''-NH_2$, $R''$ being the remnant of the molecule of the ganglioside derivative, the grafting connection of said molecule corresponding to the formula $$R_3-CH_2-NH-R''$$

$R''$ being defined as previously and $R_3-CH_2-$ representing the remnant of said polysaccharidic or modified polysaccharidic polymer when the latter has been subjected to an oxidizing cutting reaction followed by a reduction.

The porous mineral media are those already indicated above; the polysaccharidic polymer is in particular cellulose; the modified polysaccharidic polymer is in particular diethylaminoethyldextran, diethylaminoethyl starch, or diethylaminoethyl cellulose; the polysaccharidic polymer covering, modified or not, is if necessary stabilized by reticulation, the reticulating agent being such as those mentioned above.

The process for preparing these materials is characterized by the fact that a covering of the porous mineral medium is achieved by the polysaccharidic polymer or by the modified polysaccharidic polymer, that, if desired, the polysaccharidic covering is changed into a modified polysaccharidic covering, that if necessary a reticulation is made to stabilize the covering, that said polysaccharidic or modified polysaccharidic covering is subjected to an oxidizing cutting according to known methods, that the oxidation product thus obtained is made to react with the $G_{M1}$ lysoganglioside or any other $G_{M1}$ ganglioside derivative as defined above with the schematic formula $R''-NH_2$, that then the imine derivative obtained is subjected to the action of a reducing agent capable of reducing the imine bond to an amine bond.

The process described above is applicable to the products of total or partial de-acylation of the gangliosides, as these products have $NH_2$ groupings.

As indicated above, the medicine possesses interesting pharmacological properties which make it possible to use it in particular orally in the preventive or curative treatment of cholera and other acute diarrheas.

Indeed, it has been discovered that the medicine of the invention could be used orally and that it made it possible to fix the choleraic toxin as well as other bacterial toxins that may be present in the intestine.

It is known that the $G_{M1}$ ganglioside and its derivatives have an affinity in particular for the choleraic toxin. However, a therapeutic utilization of this affinity was not obvious, since it was necessary to find a particular means of administration making it possible to introduce the $G_{M1}$ in a nonsoluble form into the intestine so that the $G_{M1}$ is not absorbed by the cells of the intestinal wall, which would on the contrary promote the action of the toxin.

It was therefore especially important to find a form of administration which would allow fixing the $G_{M1}$ solidly on its insoluble medium, while keeping accessible the active sites necessary for neutralization of the toxin.

It has been found that these conditions were well met by the medicine of the invention. This medicine is stable, and the medium-ganglioside bond resists acid treatment, effervescence in an acid water medium, and the action of biliary salts. The medicine of the invention is therefore compatible with an oral therapeutic use and manifests a strong affinity for the toxins mentioned above.

The present invention also concerns a pharmaceutical composition characterized by the fact that it includes as its active principle a medicine as defined above.

The pharmaceutical composition of the invention may consist of the medicine defined above, without excipient. However, it generally contains in addition an excipient allowing it to be put into a galenical form compatible with oral administration.

Preferably, the pharmaceutical composition of the invention contains 0.1 to 20, and in particular 0.1 to 10, micromoles of gangliosides or ganglioside derivatives, approximately, per gram of composition.

These compositions may be in particular in the form of powder packets or sachets, cachets, capsules, pellets, compressed tablets (to be chewed, swallowed, or dissolved in water), drinkable suspensions, or soft capsules.

The pharmaceutical composition of the invention may also contain in addition at least one active product selected from among the intestinal antiseptics (benzonaphthol, hexamine, quinoleine), the antibiotics, the antispasmodics, etc.

The pharmaceutical composition of the invention may also contain in addition surface-active substances, physiological or not, making it possible to assure better distribution of the medicine in the digestive tract, thus increasing its effectiveness.

These pharmaceutical compositions are prepared according to the usual techniques for manufacturing galenical forms.

When the medium is activated carbon, manufacture of the galenical forms is analogous to manufacture of forms of administration containing activated carbon alone. In particular, the compressed tablets are preferably obtained by compressing a pellet containing a binder and other excipients still in the moist state, then drying the compressed tablets thus prepared.

The invention also concerns the process for preparing pharmaceutical compositions such as defined above. This process is mainly characterized by the fact that the medicine of the invention, the other active principles that may be present, and the excipient are mixed together, then the composition obtained is given the desired form according to the usual methods.

As indicated above, the medicine of the invention, in particular in the form of compositions such as defined above, may be utilized in the treatment of cholera and other acute diarrheas, either prophylactically or curatively.

The invention concerns in particular a process for treating acute diarrheas and in particular cholera, or Escherichia coli diarrheas, characterized by the fact that the medicine defined above is administered orally to a human or animal suffering or running the risk of suffering from such diarrheas.

In addition to cholera, other acute diarrheas are frequently produced by enterotoxin-producing bacteria, like certain strains of Escherichia coli, which are likely to give off in particular a thermolabile toxin the structure of which is close to the choleraic toxin and which may couple with the $G_{M1}$ ganglioside. The medicine and the treatment process of the invention can thus be effective prophylactically or curatively in particular against the Escherichia coli diarrheas.

According to a particular method of execution, the treatment process of the invention is characterized by the fact that the medicine is administered prophylactically in an amount generally corresponding to a daily administration of 2 to 50 micromoles of gangliosides or ganglioside derivatives, approximately. According to another method of execution of the treatment process of the invention, the medicine is administered curatively in an amount corresponding to a daily administration of 10 to 200 micromoles of gangliosides or ganglioside derivatives, approximately.

The dosology varies in particular according to the therapeutic effect sought (prophylactic or curative), the intensity of the diarrhetic syndrome, and the subject's age. The dosology indicated above corresponds to that which is generally effective for a human adult.

The following examples illustrate the invention, without however limiting it.

EXAMPLE 1

TECHNIQUE

From calf or beef brains an aqueous ganglioside extract is prepared. These gangliosides are purified on a Spherosil-DEAE-Dextran column as described in French patent application No. 76.23176. Elution is achieved by a 0.5 M potassium acetate pad in methanol. To this eluate is added activated carbon (CECA, WL3S quality) at 1 gram per 10 micromoles of gangliosides (or 1 to 20 micromoles). After centrifuging and washing, the coupled product is subjected to acid hydrolysis at 80° C. for 2 hours with a 0.1 M formic acid solution.

A majority of the polysialogangliosides fixed on the carbon is changed into monosialogangliosides.

After washing with a potassium bicarbonate solution and drying, a powder is obtained, hereinafter called carbon-$G_{M1}$.

PRODUCT'S CHARACTERISTICS

Aspect: Carbon powder
Identification:
1. Extraction: by boiling in a water bath for 1 hour in a chloroform/methanol/water mixture (60/30/4.5 volume to volume).
2. By chromatography in thin layers of the extract treated on a Sephadex G 25 column, which shows a principal spot corresponding to the purified $G_{M1}$.

Titration: On an aliquot of the preceding extractum, titration of the sialic acid is done according to the SVENNERHOLM method, B.B.A., 1957, 24, 604.

Activity:
Expressed in micrograms of pure standard choleraic toxin (OMS) fixed per gram of carbon-$G_{M1}$.
To determine this activity, an in-vitro or in-vivo test may be used.
In-vitro test: neutralization of a known exact level of choleraic toxin by the carbon-$G_{M1}$, then titration of the residual toxin by immunodiffusion (MANCINI technique) and/or by hemagglutination (agglutination of red lamb corpuscles covered with $G_{M1}$).
In-vivo test: neutralization of a known exact level of choleraic toxin by carbon-$G_{M1}$ and innoculation of the suspension into the ileal loop of a rabbit (classic rabbit ileal loop technique).

Stability: Kept in closed flask at room temperature. The product is stable. The product is not affected by being kept at 50° C. The carbon-$G_{M1}$ bond is not affected by acid or alkaline pH conditions nor by the action of biliary salts.

EXAMPLE 2

Preparation of vermiculated pellets

Composition:
Carbon-$G_{M1}$ powder: 100 g
Icing sugar: 740 g
Simple syrup (approximately): 250 g Icing sugar and carbon are mixed in a mortar; little by little the syrup is added to obtain a paste which yields vermiculated pellets when passed through a strainer.

EXAMPLE 3

Preparation of pellets

Composition:
Carbon-$G_{M1}$ powder: 50 g
Saccharose: 44 g
Gum arabic: 6 g

While being stirred the carbon is moistened with a syrup made from 70 g of purified water, 44 g of saccharose and 6 g of gum arabic. This is granulated and oven-dried at 50° C.

The gum arabic acts as a binder. In its place one of the many commercial pregelatinized starches can be used, modified or not.

EXAMPLE 4

Preparation of compressed tablets

Composition:
Carbon-$G_{M1}$ powder: 40 g
Saccharose: 54 g
Pregelatinized corn starch: 6 g The carbon-$G_{M1}$ is placed in a mortar and moistened with a syrup containing 60 ml of water, 54 g of saccharose and 6 g of pregelatinized starch. This is granulated and partially dried at 50° C. in a ventilated oven for about 1 hour. The pellets are compressed while still slightly moist. The compressed tablets obtained are dried at 50° C. for 18 hours.

This produces very hard, not very friable pellets which disintegrate in less than 15 minutes according to the test protocol of the French Pharmacopeia, 9th edition.

EXAMPLE 5

Administering the medicine

A composition based on carbon-$G_{M1}$ containing 5 micromoles of $G_{M1}$ per gram is used. Prophylactically, this composition is administered at 2 g per day. Curatively, during acute diarrhea, 1 g is administered every 1 to 2 hours, then 1 g every 4 to 6 hours.

EXAMPLE 6

Preparation of Cellulose-$G_{M1}$ sachets or capsules

Composition:
Cellulose-$G_{M1}$: 70 g
Icing sugar: 29 g
Magnesium stearate: 1 g

Mix dry, then distribute in sachets or capsules.

The cellulose-$G_{M1}$ contains one micromole per gram capable of neutralizing up to 6 mg of choleraic toxin per gram.

EXAMPLE 7

Preparation of Cellulose-$G_{M1}$ compressed tablets

Compress the cellulose-$G_{M1}$ powder to prepare flat tablets 30 mm in diameter. Crush them to obtain a 300 $\mu$m passing through a strainer. Add 1% magnesium stearate. Compress to obtain convex tablets 10 mm in diameter.

The cellulose-$G_{M1}$ is the same as in example 6.

EXAMPLE 8

Preparation of cellulose-$G_{M1}$ compressed tablets

Moisten the cellulose-$G_{M1}$ powder (analogous to that in example 6) with a 20% aqueous solution of PEG 6000 in purified water to provide 2.5% of PEG to 97.5% of cellulose-$G_{M1}$ in dry extract. Pass the moist mixture through a ganulating device. Dry the pellets obtained. Weigh and add 1% of its weight of magnesium stearate.

From this mixture prepare convex tablets 10 mm in diameter.

EXAMPLE 9

Examples or preparing partial de-acylation derivatives of $G_{M1}$ 9.1. Activation of the $G_{M1}$ ganglioside 5 micromoles of $G_{M1}$ are dissolved in 1 ml of N soda, and the solution is incubated at 80° C. for 2 hours. The solution may then be diluted and adjusted for coupling the activated ganglioside according to any of the methods described below.

The product obtained yields a positive reaction in the ninhydrine test, the coloring observed being however less intense than that observed with the $G_{M1}$ lysoganglioside.

9.2. Activation of the $G_{M1}$ ganglioside 10 micromoles of $G_{M1}$ are dissolved in 10 ml of N/10 soda and the solution is incubated at 40° C. for 15 hours. The solution is then ready for the coupling of the activated ganglioside according to any of the methods described below. The ninhydrine test and the SANGER test are positive. In the case of coupling on an epoxy medium, this medium may advantageously be added at the start of the alkaline treatment. Activation of the ganglioside and its fixation onto the medium are then done at the same stage at the same pH.

9.3. Coupling of the ganglioside thus activated onto a polysaccharidic matrix by means of a bifunctional agent with epoxy functions.

Cellulose may for example be used. The coupling by means of a diepoxy agent—for example, 1–4 butanedioldiglycidylether (Aldrich)—can be done by incubating for one night at room temperature 10 g of cellulose in a mixture containing 20 ml of NaOH N, 20 ml of butanedioldiglycidylether and 40 mg of $NaBH_4$.

The following day the medium is washed in alcohol, water, and finally 0.1 N soda. After drying by filtration, the medium is placed in contact for one night with the previously activated ganglioside and in a solution of the 0.1 N soda. A dose of 1 to 10 $\mu$mole/ml is recommended. An incubation temperature of 20° to 40° C. is preferable.

9.4. Coupling of the $G_{M1}$ ganglioside thus activated onto a polysaccharidic matrix oxidized by soldium periodate.

For this method, the cellulose or the porous media impregnated with polysaccharides such as those in the French patent application No. 76.23176 are preferable. Agarose is in fact hardly oxidized under the same conditions.

This method has already been applied (see French patent application No. 77.28163) for coupling lysogangliosides prepared according to the TAKETOMI method.

The conditions for fixing the activated gangliosides by partial de-acylation are identical.

10 g of medium (for example cellulose) are added to 100 ml of 0.02 M sodium periodate for 2 hours at room temperature.

The medium is then washed in a solution of 0.02 M pH 9 sodium carbonate with 10 g/l NaCl added, dried by filtration and added to 15 ml of a pH 9 solution of gangliosides activated according to any of the examples 9.1 and 9.2. above. A dose of 1 to 10 $\mu$mole/ml of medium is recommended.

After incubation for one night at room temperature, $NaBH_4$ sodium borohydride is added for 2 hours at 20° C. (0.2 M finally) to reduce the imine bonds formed into extremely stable amine bonds.

9.5. Coupling of the $G_{M1}$ ganglioside thus activated onto a polysaccharidic matrix by the cyanogen bromide method.

The method is that described by PORATH et al., Nature, 215, 1491 (1967). In practice, it is sufficient to mix the activated sepharose with the cyanogen bromide, marketed by PHARMACIA (Uppsala, Sweden), at pH 11 following the instructions. A dose of 1 to 10 $\mu$mole of activated ganglioside per ml of gel is also recommended here. It is possible to adapt this technique to cellulose or to the porous mineral media previously described without changing in any way the operating conditions.

9.6. Study of fixation of the choleraic toxin by the medicine of the invention

The porous mineral medium is silica such as that marketed by RHONE-POULENC under the name of SPHEROSIL XOC 005. Its specific surface is about 10 $m^2/g$, its pore diameter is about 300 nm; this silica is impregnated with a monomolecular layer of DEAE Dextran and reticulated according to the process described in French patent application No. 76.23176. By applying the method described in examples 9.3., 9.4., or 9.5. above to 1 g of this medium, it is possible to fix for example 5 $\mu$mole of $G_{M1}$ ganglioside previously activated by de-acylation according to the examples 9.1. or 9.2. above.

This medium is then washed with 0.1 N soda and put in the column. The column is balanced in a solution containing 0.05 M sodium citrate at pH 7 with 10 g/l of NaCl added. A culture filtrate of "Vibrio cholerae INABA 569 B" containing in the raw state 25 $\mu$g/ml of choleraic toxin is dialysed against the same pad. 500 ml of this impure choleraic toxin solution are then filtered in the column. All impurities not recognizing the $G_{M1}$ ganglioside pass through the column. Only the choleraic toxin is fixed in the column and can be recovered by elution with 0.05 M citric acid, pH 2.8. The product recovered contains about 100% of the biological activity present in the initial culture. The choleraic toxin thus recovered (12.5 mg) appears identical to that prepared according to the process described in French patent application No. 77.28163.

Likewise, fixation of the $G_{M1}$ ganglioside was achieved according to the same method on other media made from agarose or cellulose.

We claim:

1. A medicament for the treatment of acute diarrhea comprising an orally administrable medium having fixed thereon an effective amount of a ganglioside or ganglioside derivative having an affinity for the toxins produced by bacteria responsible for diarrhea, said medium having a strong affinity for the gangliosides or which can be chemically linked to the said ganglioside or ganglioside derivative, said medium further having a high specific surface, and allowing satisfactory contact between the ganglioside and the toxin to be neutralized.

2. The medicament of claim 1 wherein said medium is activated carbon, latex, a polysaccharide, modified or not, a porous mineral medium or a porous mineral medium coated with a polysaccharide, modified or not.

3. The medicament of claim 1 wherein said ganglioside or ganglioside derivative is selected from the group consisting of $G_{M1}$ ganglioside, $G_{M1}$ lysoganglioside, the product of partial hydrolysis of $G_{M1}$ ganglioside and mono- or a-sialo ganglioside resulting from acid treatment of said ganglioside or ganglioside derivative.

4. The medicament of claim 1 wherein said medium consists of particles of activated carbon.

5. The medicament of claim 1 wherein said ganglioside derivative is a product of partial de-acylation of a ganglioside.

6. The medicament of claim 5 wherein said partial de-acylation product is a derivative of $G_{M1}$ ganglioside.

7. The medicament of claim 1 wherein said ganglioside derivative is $G_{M1}$ lysoganglioside.

8. The medicament of claim 1 wherein said medium is a polysaccharide, modified or not.

9. The medicament of claim 2 wherein said polysaccharide is cellulose.

10. The medicament of claim 1 wherein said ganglioside or ganglioside derivative is present in an amount of 1 to 20 micromoles per gram of said medium.

11. The medicament of claim 1 wherein said ganglioside or ganglioside derivative is present in an amount of 3 to 10 micromoles per gram of said medium.

12. A pharmaceutical composition for the treatment of acute diarrhea comprising, as the active principle, an effective amount of the medicament of claim 1.

13. The pharmaceutical composition of claim 12 which also includes a pharmaceutically acceptable, orally administrable excipient.

14. The pharmaceutical composition of claim 12 which contains from 0.1 to 20 micromoles of ganglioside or ganglioside derivative per gram of said composition.

15. The pharmaceutical composition of claim 12 which contains from 0.1 to 10 micromoles of ganglioside or ganglioside derivative per gram of said composition.

16. The pharmaceutical composition of claim 12 which also includes an effective amount of at least one other active principle selected from an intestinal antiseptic, an antibiotic or an antispasmodic.

17. The pharmaceutical composition of claim 12 which also includes an effective amount of a surface-active agent.

18. A process for the preparation of the medicament of claim 1 comprising contacting a solution of said ganglioside with said medium so as to fix said ganglioside on said medium and thereafter subjecting the ganglioside fixed on said medium to acid hydrolysis whereby a majority of the polysialogangliosides are transformed into monosialogangliosides.

19. The process of claim 18 wherein said ganglioside is $G_{M1}$ ganglioside.

20. The process of claim 18 wherein said medium consists of particles of activated carbon.

21. A process for the treatment of acute diarrhea comprising orally administering to a human or animal suffering from or running the risk of said diarrhea an effective amount of the medicament of claim 1.

22. The process of claim 21 wherein said medicament is administered prophylactically in an amount corresponding to a daily administration of approximately 2 to 50 micromoles of said ganglioside or ganglioside derivative.

23. The process of claim 21 wherein said medicament is administered curatively in an amount corresponding to a daily administration of approximately 10 to 200 micromoles of said ganglioside or ganglioside derivative.

* * * * *